United States Patent [19]
Winkler

[11] Patent Number: 5,345,362
[45] Date of Patent: Sep. 6, 1994

[54] PORTABLE COMPUTER APPARATUS WITH ARTICULATING DISPLAY PANEL

[75] Inventor: Thomas J. Winkler, Isanti, Minn.

[73] Assignee: Medtronic, Inc., Minneapolis, Minn.

[21] Appl. No.: 55,072

[22] Filed: Apr. 29, 1993

[51] Int. Cl.⁵ .......................... H05K 7/16; G06F 1/16
[52] U.S. Cl. .................................... 361/681; 248/923; 248/456
[58] Field of Search .................. 40/606; 248/917-923, 248/456, 465; 312/223.2, 226; 345/905; 364/708.1; 361/679, 681-683

[56] References Cited

U.S. PATENT DOCUMENTS

| | | |
|---|---|---|
| Re. 32,361 | 2/1987 | Duggan . |
| D. 295,631 | 5/1988 | Wells-Papanek et al. . |
| D. 295,632 | 5/1988 | Wells-Papanek et al. . |
| 4,208,008 | 6/1980 | Smith . |
| 4,233,985 | 11/1980 | Hartlaub et al. . |
| 4,236,524 | 12/1980 | Powell et al. . |
| 4,250,884 | 2/1981 | Hartlaub et al. . |
| 4,253,466 | 3/1981 | Hartlaub et al. . |
| 4,273,132 | 6/1981 | Hartlaub et al. . |
| 4,273,133 | 6/1981 | Hartlaub et al. . |
| 4,374,382 | 2/1983 | Markowitz . |
| 4,556,063 | 12/1985 | Thompson et al. . |
| 4,739,316 | 4/1988 | Yamaguchi et al. ......... 312/223.2 X |
| 4,903,222 | 2/1990 | Carter et al. . |
| 4,960,256 | 10/1990 | Chihara et al. ................. 361/681 X |
| 4,976,007 | 12/1990 | Lam . |
| 5,016,849 | 5/1991 | Wu . |
| 5,052,078 | 10/1991 | Hosoi . |
| 5,090,913 | 2/1992 | Kobayashi . |
| 5,168,426 | 12/1992 | Hoving et al. ....................... 361/683 |
| 5,200,913 | 4/1993 | Hawkins et al. .................... 361/681 |
| 5,249,103 | 9/1993 | Forsythe ........................ 361/681 X |
| 5,257,164 | 10/1993 | Perez et al. ......................... 361/681 |
| 5,267,123 | 11/1993 | Boothroyd et al. ............ 361/681 X |

FOREIGN PATENT DOCUMENTS 4-218820  8/1992  Japan ............................. G06F 1/16

OTHER PUBLICATIONS

*PC World Magazine*, p. 51, Dec. 1992.
"Sales Brochure" for GVO Inc., 2470 Embardacero Way, Palo Alto, Calif. 94303, 415.858.2525, No Date Given.

Primary Examiner—Leo P. Picard
Assistant Examiner—Michael W. Phillips
Attorney, Agent, or Firm—Reed A. Duthler; Harold R. Patton

[57] ABSTRACT

A portable computer apparatus having a dual-pivot articulating display screen capable of being adjusted to a plurality of different viewing angles as desired. In the preferred embodiment, the disclosed apparatus is an implantable medical device programming unit. The substantially flat display screen is movable from a closed position in which it is substantially parallel with an upper surface of the apparatus, to any of a plurality of open positions wherein the display can be viewed by an operator. The display screen is coupled to the main housing of the apparatus by means of a pivoting link arm, and the central portion of the bottom edge of the display screen is provided with a support member extending therefrom, which may be located in one of a number of defined locations within a support channel in the upper surface of the main housing of the apparatus. The display is preferably touch sensitive, so that user interaction with the apparatus is accomplished by a stylus or the like. The disclosed apparatus is provided with an internal ECG strip-chart printer. A compartment in the apparatus is provided for storage of a magnetic programming head, the touch-sensitive screen stylus, and patient ECG cables. A separate compartment is provided for storage of an AC power cord.

8 Claims, 9 Drawing Sheets

PORTABLE COMPUTER APPARATUS WITH ARTICULATING DISPLAY PANEL

FIELD OF THE INVENTION

This invention relates to the field of portable computer equipment, and more particularly relates to a portable computer apparatus having an articulating display panel.

BACKGROUND OF THE INVENTION

Substantial technological improvement in the field of electronics over past years has enabled computer equipment manufacturers to provide powerful, fully-featured computers that are compact and portable. So-called "laptop" or "notebook" type computers have proven to be extremely popular in recent years, and a wide variety of such computers are known and commercially available.

A portable computer apparatus will typically have at least some subset of the following components: a housing for containing the computer circuitry and other electronic components; a power source (e.g., a battery) or at least a cable for connecting the apparatus to a source of power; at least one means for accepting user input (e.g., an alphanumeric keyboard, a "mouse", or the like); and output means (e.g., a text and/or graphic display, a printer, or the like) for communicating information to the user. In addition, portable computer equipment will frequently be equipped with data storage devices, such as a floppy disk drive or a hard disk drive. While some set of these components can be found in any portable computer equipment, there is a nearly endless variety of ways that they can be arranged.

There are a number of design considerations that are of particular concern in the context of portable computer equipment. In general, it is preferable for a portable computer apparatus to be durable and ruggedly constructed, since it should be expected that a portable computer will be picked up, carried about, jostled, and even dropped occasionally. Moreover, while the size and weight of portable computer equipment is preferably kept to a minimum, this is preferably not achieved at the expense of making components like the display, keyboard, or battery too small, or at the expense of making structural components weak and easily broken.

Ergonomic factors should also be considered in the design of portable computer equipment. For example, some portable computers, such as the Compaq SLT, are provided with detachable keyboards so that a user can position the keyboard conveniently for typing without having to move the entire computer. Also, portable computers often are equipped with a display screen that can be manipulated into a variety of orientations so that it can be easily viewed by the user from different angles. This is particularly important with liquid-crystal displays (LCDs), which are typically more difficult to view at oblique angles.

One common way in which portable computer manufacturers satisfy the requirements of portability, ruggedness, and ergonomic convenience is by providing a hinged display screen that can be folded down and secured onto the top of the computer housing, thereby protecting the screen and reducing the size of the apparatus when not in use. When opened, the hinged display screen can be adjusted over a range of viewing angles so that the user can select a convenient one. As a further expedient, the closed hinged display can serve as a protective structure for other components, such as the keyboard. Such a configuration is described in U.S. Pat. No. 4,903,222 to Carter et al. entitled "Arrangement of Components in a Laptop Computer System", which patent is incorporated herein by reference in its entirety.

A portable computer having an hinged display screen which folds down over an alphanumeric keyboard is also disclosed in U.S. Pat. No. 5,090,913 to Kobayashi; in U.S. Pat. No. 5,016,849 to Wu; in U.S. Pat. No. 5,052,078 to Hosoi; in U.S. Pat. No. 4,976,007 to Lam; and in U.S. Pat. No. 4,960,256 to Chihara et al.

In addition to the various types of general-purpose portable computer equipment that are known and commercially available, there are also many different types of special-purpose, portable computer devices. Such devices may have many of the same components found in general-purpose computers, but may also have additional components, depending upon the specialized purpose for which they are intended. The class of special-purpose portable computer equipment may include such devices as service or test equipment carried by field service technicians; data storage and acquisition carried by delivery persons, meter-readers and the like; portable communications devices; and of particular relevance to the present invention, computerized programmers for implantable medical devices and the like.

Implantable medical devices, such as cardiac pacemakers, cardiac defibrillators, neural stimulators, and the like, are often programmable in their operation by means of a radio-frequency telemetry link established between the device and an external programmer unit. In the case of cardiac pacemakers, for example, a clinician may, through the use of an external programmer, control such parameters as pacing rate, pacing mode, sensitivity, pacing output, and the like, in a pacemaker implanted in a patient. Pacemaker programmers are preferably portable, so that they may be conveniently transported from patient to patient in a hospital, or even taken to a patient's home or to another non-hospital setting. Portability is also desirable due to the possibility that the programmer may be needed in an emergency situation, e.g., when the patient is undergoing surgery in an operating room. A variety of different programmable pacemakers, and external programming units therefor, are known and commercially available.

A programmer for non-invasively programming a cardiac pacemaker is described in its various aspects in the following U.S. Patents to Hartlaub et al., each commonly assigned to the assignee of the present invention and each incorporated by reference herein: U.S. Pat. No. 4,250,884 entitled "Apparatus For and Method Of Programming the Minimum Energy Threshold for Pacing Pulses to be Applied to a Patient's Heart"; U.S. Pat. No. 4,273,132 entitled "Digital Cardiac Pacemaker with Threshold Margin Check"; U.S. Pat. No. 4,273,133 entitled Programmable Digital Cardiac Pacemaker with Means to Override Effects of Reed Switch Closure"; U.S. Pat. No. 4,233,985 entitled "Multi-Mode Programmable Digital Cardiac Pacemaker"; and U.S. Pat. No. 4,253,466 entitled "Temporary and Permanent Programmable Digital Cardiac Pacemaker".

Aspects of the programmer that is the subject of the foregoing Hartlaub et al. patents (hereinafter "the Hartlaub programmer") are also described in U.S. Pat. No. 4,208,008 to Smith, entitled "Pacing Generator Programming Apparatus Including Error Detection Means" and in U.S. Pat. No. 4,236,524 to Powell et al., entitled "Program Testing Apparatus". The Smith '008 and Powell et al. '524 patents are also incorporated by reference herein in their entirety.

A telemetry system for communicating information, either in analog or digital form, between an implanted device and an external programming apparatus is disclosed in U.S. Pat. No. 4,374,382 to Markowitz entitled "Marker Channel Telemetry System for a Medical Device", and in U.S. Pat. No. 4,556,063 to Thompson et al., entitled "Telemetry System for a Medical Device". The Markowitz '382 and Thompson et al. '063 patents are commonly assigned to the assignee of the present invention and are both hereby incorporated by reference in their entirety.

Implanted devices in general have improved in their sophistication and functionality over the past years, and it has become increasingly more important for a physician or clinician to be able to interrogate the device to determine its operational status, and to be able to communicate numerous commands and parameters to the device in order to control various aspects of the device's operation. Improvements in the telemetry system, as reflected, for example, in the above-reference Thompson '063 patent, have enabled a great deal of information to be readily and quickly exchanged between the implanted device and the external programming unit. In some cases, a real-time electrocardiogram (ECG) signal may be transmitted from the implanted device to an external unit, so that the physician can monitor the patient's heart activity and the effects of pacing pulses thereon. A pacemaker system having such capability is described, for example, in U.S. Pat. No. Re. 32,361 to Duggan, entitled "Implantable Telemetry Transmission System for Analog and Digital Data", assigned to the assignee of the present invention and incorporated into the present disclosure by reference in its entirety.

Given the level of sophistication and functionality of state-of-the-art pacemakers, it has become necessary for the operational capability of external programming units for such pacemakers to be similarly improved. For example, since pacemakers are known which are capable of transmitting real-time ECG signals to an external unit, it would naturally be desirable for the external unit to be able to visually display the ECG signal, without the need for additional wiring or equipment.

In addition to the above-discussed considerations that should be taken into account in designing a portable, general-purpose computer, there are certain factors that are of particular importance in the context of medical device programming units. A medical device programming unit should be simple to operate, highly reliable, and well adapted for use in an operating room or other clinical setting.

SUMMARY OF THE INVENTION

The present invention relates to a portable computer apparatus, and in particular relates to a portable, computer-based external programming unit for implantable medical devices.

In accordance with one embodiment of the invention, a portable computer apparatus is provided which has a dual-pivot articulating display screen which can be readily adjusted into a plurality of viewing angles, and which folds down to a closed, latched position on top of the computer apparatus when the apparatus is not being used or is being transported.

In the preferred embodiment, the apparatus is especially designed to function as a programming unit for implantable medical devices, such as pacemakers, defibrillators, and the like. As such, it is equipped with an internal ECG strip-chart printer, as well as a magnetic programming head used in establishing a telemetry link with implanted devices.

In accordance with the present invention, the disclosed computer apparatus is further provided with a touch-sensitive screen actuable by means of a stylus. The touch-sensitive screen serves as the principal means of user interaction with the apparatus, so that the need for a separate keyboard or other user-input means is generally obviated.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein.

DETAILED DESCRIPTION OF A SPECIFIC EMBODIMENT OF THE INVENTION

Figure 1:
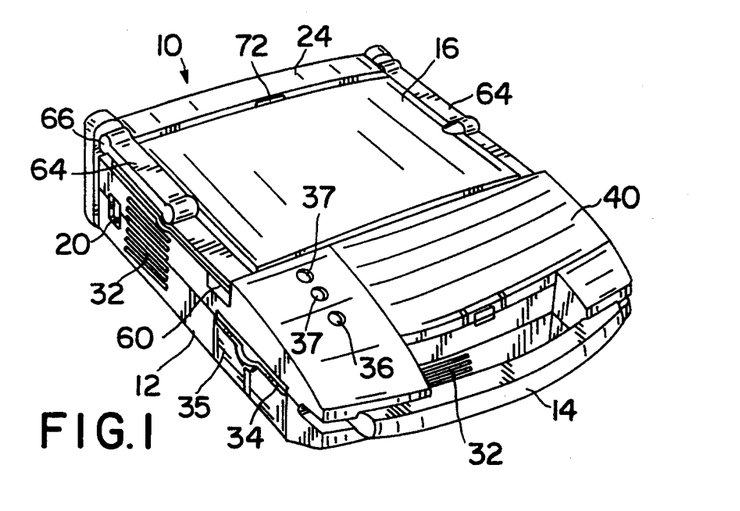
FIG. 1 is a front perspective view of a portable computer apparatus in accordance with one embodiment of the present invention.
Figure 2:
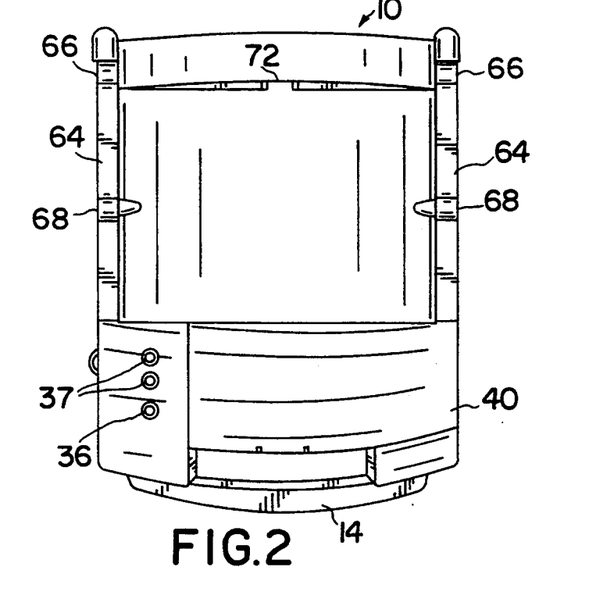
FIG. 2 is a top view of the apparatus from FIG. 1.
Figure 3:
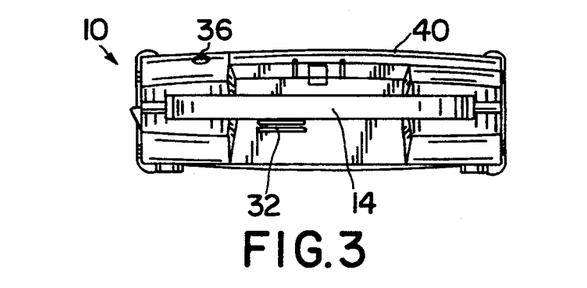
FIG. 3 is a front view of the apparatus from FIG. 1.
Figure 6:
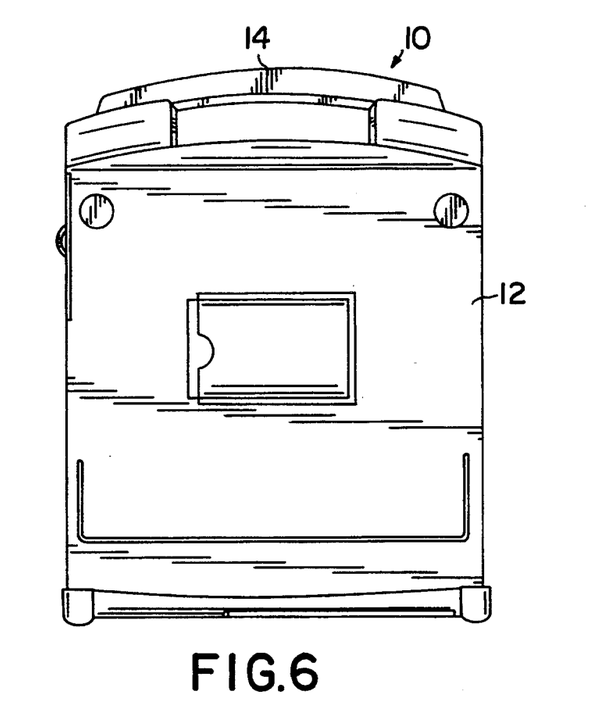
FIG. 6 is a bottom view of the apparatus of FIG. 1.
Figure 7:
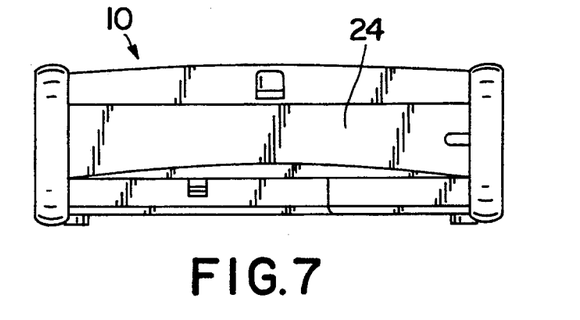
FIG. 7 is a rear view of the apparatus of FIG. 1.
Figure 8:
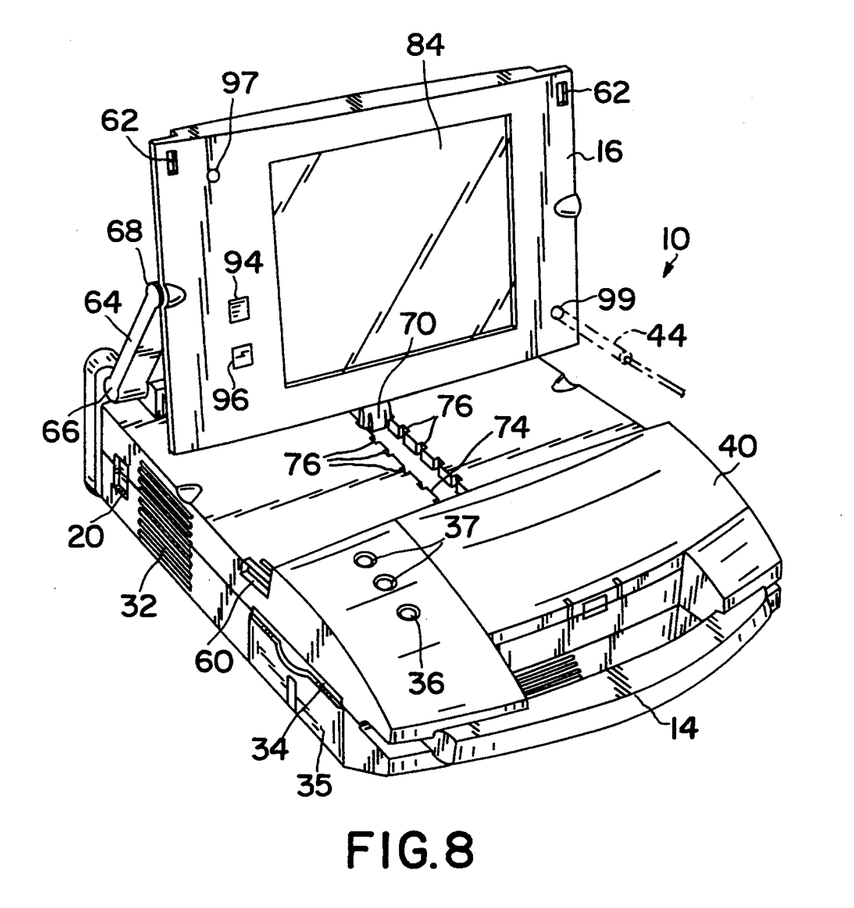
FIG. 8 is a front perspective view of the apparatus of FIG. 1 with the display screen opened into one of its viewing positions.
Figure 9:
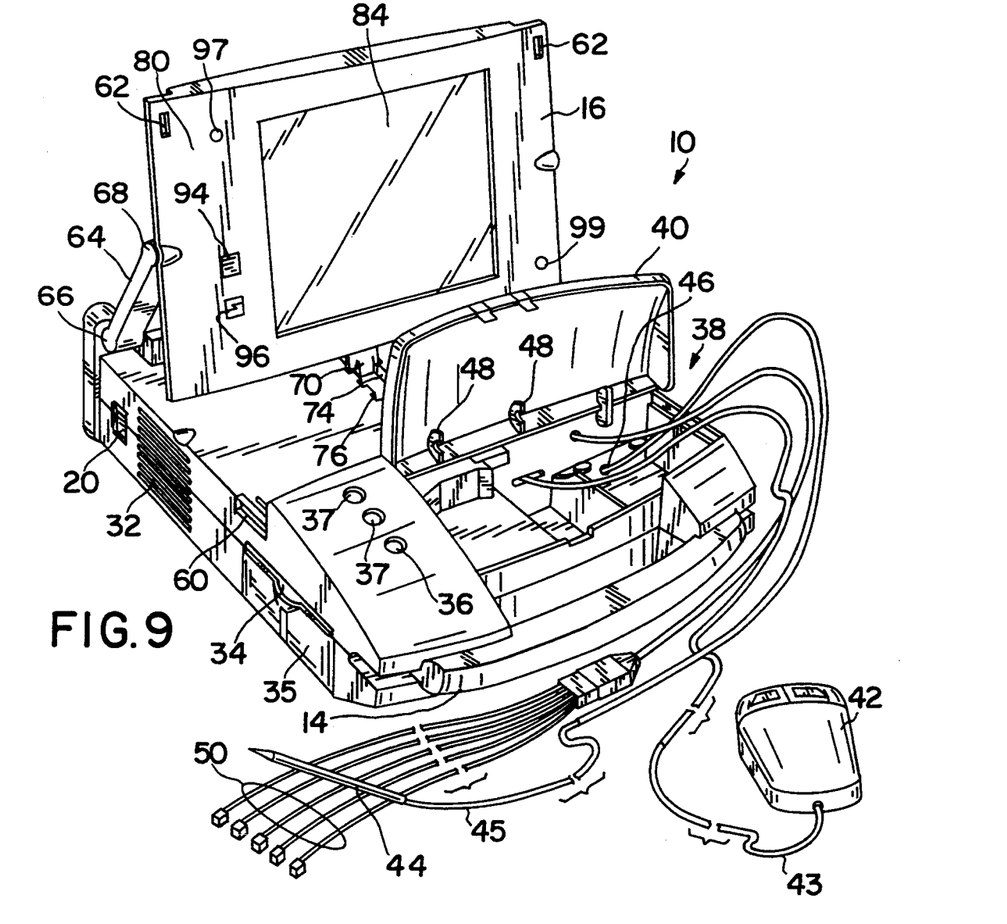
FIG. 9 is a front perspective view of the apparatus of FIG. 1 showing the contents of a storage compartment therein.
Figure 10:
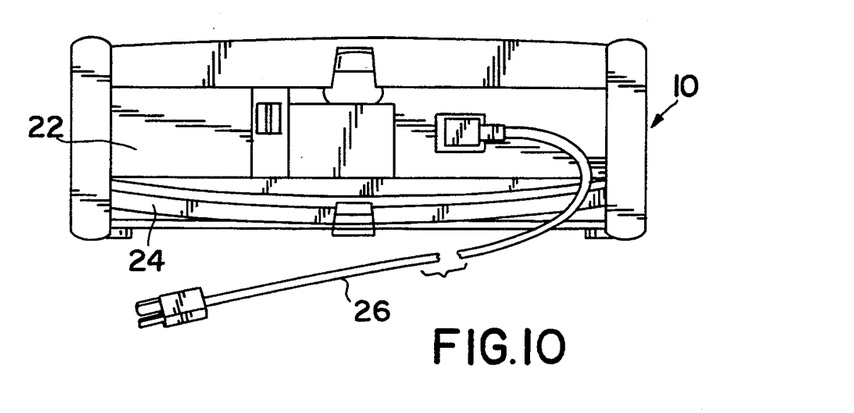
FIG. 10 is a rear view of the apparatus of FIG. 1 showing a power cable compartment therein.

A presently preferred embodiment of the invention is illustrated from various perspectives in FIGS. 1 through 13, in order that various features of the invention can be shown. FIGS. 1, 8, and 9 are front perspective views of apparatus 10. FIG. 2 is a top view of apparatus 10. FIG. 3 is a front view, FIGS. 4, 5, 11, 12, and 13 are side views, FIG. 6 is a bottom view, and FIGS. 7 and 10 are rear views.

In the presently preferred embodiment of the invention, apparatus 10 is a computer device for programming implantable medical devices such as pacemakers, defibrillators, and the like; as such, there are several specialized components incorporated into the apparatus, as will be hereinafter described in greater detail. Internally, programmer 10 includes a processing unit (not shown in the Figures) which in accordance with the presently disclosed embodiment of the invention is a personal computer type motherboard, e.g., a computer motherboard including an Intel 80386 microprocessor and related circuitry such as digital memory. The details of design and operation of the computer system will not be set forth in detail in the present disclosure, as it is believed that such details are not necessary for an appreciation of the present invention. For the purposes of the present disclosure, it suffices to state that programmer 10 is capable of performing at least the types of operations described in the above-referenced Hartlaub et al. programmer patents.

Programmer 10 comprises an outer housing 12, which is preferably made of thermal plastics or another suitably rugged yet relatively light-weight material. A carrying handle, designated generally as 14 in the Figures, is integrally formed into the front of housing 12. With handle 14, programmer 10 can be carried like a briefcase.

In accordance with one aspect of the present invention, an articulating display screen 16 is disposed on the upper surface of housing 12. As shall hereinafter be described in greater detail, display screen 16 folds down into a closed position (shown, for example, in FIG. 1), when programmer 10 is not in use, thereby reducing the size of programmer 10 and protecting the display surface of display 16 during transportation and storage thereof.

Programmer 10 has dimensions of approximately 46-cm × 36-cm × 13-cm, and weighs approximately 8.4-kg.

Figure 5:
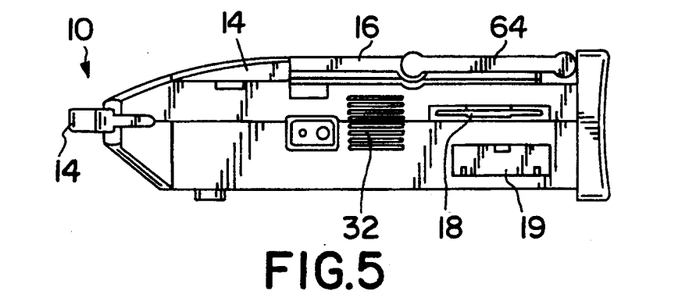
FIG. 5 is a right side view of the apparatus of FIG. 1.

Referring to FIG. 5, a floppy disk drive is disposed within housing 12 and is accessible via a disk insertion slot designated as 18 in the Figures. A hard disk drive is also disposed within housing 12, and it is contemplated that a hard disk drive activity indicator, (e.g., an LED, not shown in the Figures) could be provided to give a visible indication of hard disk activation.

As would be appreciated by those of ordinary skill in the art, it is often desirable to provide a means for programmer 10 to adapt its mode of operation depending upon the type of implanted device to be programmed. Accordingly, it may be desirable to have an expansion cartridge containing EPROMs or the like for storing program information to control programmer 10 to operate in a particular manner corresponding to a given type of implantable device. As shown in FIG. 5, a hinged expansion slot cover 19 is provided on the right side of programmer 10. Cover 19 opens to allow insertion of such an expansion cartridge or the like (not shown).

Referring to FIG. 10, a compartment 22 having a hinged cover 24 is provided for storing a power cord 26 when programmer 10 is not in use.

Air vents 32 (shown in FIGS. 1, 3, 4, 5, and 8, for example) are provided at various points in housing 12, so that an internal fan (not shown) can circulate air within housing 12 and prevent overheating of components therein. In addition, a printer output slot 34 (see FIGS. 1 and 4, for example) is disposed on the left side of housing 12. In accordance with the presently preferred embodiment of the invention, programmer 10 is equipped with an internal strip-chart printer (not shown) so that a hard-copy of a patient's ECG can be generated when the ECG signal is telemetered to the programmer 10 over the above-described telemetry channel. Several types of ECG printers, such as the AR-100 printer available from General Scanning Co., are known and commercially available. A printer control button 36 and printer speed control buttons 37 are disposed on the upper surface of housing 12 so that the printer can be activated and the speed of strip-chart output selected. Buttons 36 and 37 are preferably of the well-known membrane type or are otherwise sealed such that external moisture and dirt are repelled.

Figure 4:
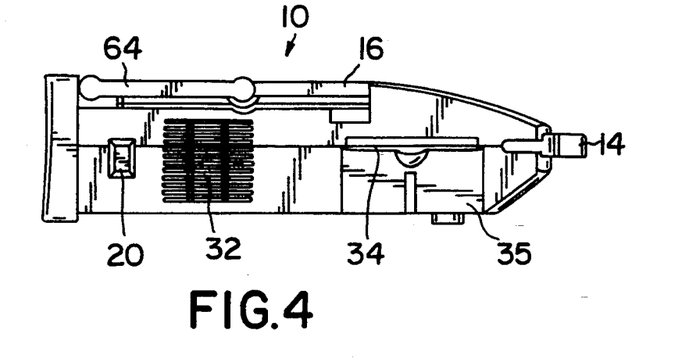
FIG. 4 is a left side view of the apparatus from FIG. 1.

A hinged cover 35 can be opened to provide access to the internal printer mechanism, e.g., to supply the printer with paper. Also shown in FIGS. 1 and 4 is a power switch 20 which is preferably inset slightly with respect to housing 12, such that the likelihood of accidentally turning programmer 10 off is minimized.

In the perspective view of FIG. 8, programmer 10 is shown with articulating display screen 16 having been lifted up into one of a plurality of possible open positions such that the display area thereof is visible to a user situated in front of programmer 10. Articulating display screen is preferably of the LCD or electroluminescent type, characterized by being relatively thin as compared, for example, a cathode ray tube (CRT) or the like. In the presently preferred embodiment of the invention, display screen 16 is one manufactured by and commercially available from Planar Systems, Inc.

As would be appreciated by those of ordinary skill in the computer art, display screen 16 is operatively coupled to the computer circuitry disposed within housing 12 and is adapted to provide a visual display of graphics and/or data under control of the internal computer.

In accordance with one aspect of the present invention, display screen 16 is provided with touch-sensitive capability, such that a user can interact with the internal computer by touching the display area of display screen 16 with a stylus, or even the user's finger. It is believed that those of ordinary skill in the computer art will be familiar with touch-sensitive display technology, and the details of implementation of such a display will not be described further herein. Touch-sensitive display screen 16 is the primary input medium for programmer 10, and therefore preferably has sufficient resolution to support stylus operations including selection, gestures, annotation, and character recognition.

Referring to FIG. 9, a compartment 38 with a hinged cover 40 is provided generally near the front of programmer 10. Compartment 38 is used for storage of a programming head 42 which, as would be appreciated by those of ordinary skill in the art, is placed over a patient's body near the implant site of an implanted device, in order to establish a telemetry link between the implanted device and the programmer. Such a programming head is disclosed, for example, in the above-reference Hartlaub programmer patents. Programming head 42 is coupled to internal circuitry of programmer 10 via a cable 43.

Compartment 38 is also used for storage of a stylus 44 used to interact with touch screen 16. Stylus 44 is coupled to circuitry within housing 12 via a cable 45 that is coupled to programmer 10 by means of a coaxial connector 46. Clips 48 are preferably provided on the underside of hinged cover 40 for holding stylus 44 when not in use.

Compartment 38 is also used for storage of a plurality patient cables 50 for obtaining a patient's surface ECG. Patient cables 50 convey a patient's surface ECG to internal circuitry of programmer 10, so that the surface ECG can be displayed on display screen 16 or printed out on the internal ECG printer, previously described.

When display screen 16 is folded into its closed position (see, for example, FIG. 1), it is secured in place by means of latching mechanisms 60 disposed on the left and right sides of housing 12. Latching mechanisms 60 are adapted to be engaged in corresponding recesses 62 disposed on the front surface of display screen 16, and are spring-biased to remain engaged therein until they are simultaneously actuated by pressing inward from the respective right and left sides of programmer 10. To open display screen 16, latching mechanisms 60 are depressed inwardly, thereby becoming disengaged from recesses 62. Latching mechanisms 60 prevent display screen 16 from opening during transportation and storage of programmer 10. Latching mechanisms 60 are further adapted to automatically re-engage recesses 62 when screen 16 is folded down to its closed position, so that no manual actuation of latches 60 is necessary to close screen 16.

Referring to FIGS. 1 and 8, it can be seen that display screen 16 is supported by left and right link arms 64. Link arms 64 are each pivotally secured at one end onto the upper surface of housing 12, at stationary pivot points designated 66. In addition, and in accordance with another aspect of the present invention, link arms 64 are each pivotally secured at another end to the respective sides of display screen 16, at the moving pivot points designated 68. The dual-pivot articulating configuration of display screen 16 and link arms 64 affords a large degree of adjustability of display screen 16, as shall be hereinafter described in further detail.

A screen support member 70 is rigidly disposed on the bottom edge of display screen 16. Display screen 16 rests upon support member 70 when display screen 16 is in any of its possible open positions. When display screen 16 is in the closed position, support member 70 is received in a recess 72 integrally formed into the upper surface of housing 12.

When display screen 16 is lifted up into on of its open positions, support member 70 rests at some point within a graduated support channel 74, as shown in FIG. 8. Support channel 74 extends from substantially proximal to the front of the upper surface of housing 12 towards the back, and in the presently preferred embodiment of the invention is integrally formed into the upper surface of housing 12. A plurality of spaced-apart indentations 76 are defined in the sides of channel 74. Indentations 76 are provided so that the distal end of support member 70 can be received in channel 74, preventing support member 70 from sliding back and forth therein. Indentations 76 are disposed at points of varying distance from the front of programmer 10. The viewing angle of display screen 16 when in the open position depends upon which of the indentations 76 engage support member 70. Of course, the number of possible viewing angles is determined by the number and spacing of indentations 76 defined in channel 74.

Viewing angle adjustment of display screen 16 is accomplished by lifting screen 16 up slightly so that support member 70 is disengaged from support channel 74. Then, screen 16 can be freely pivoted to a desired position and lowered down such that support member 70 is engaged by a corresponding pair of indentations 76.

Figure 11:
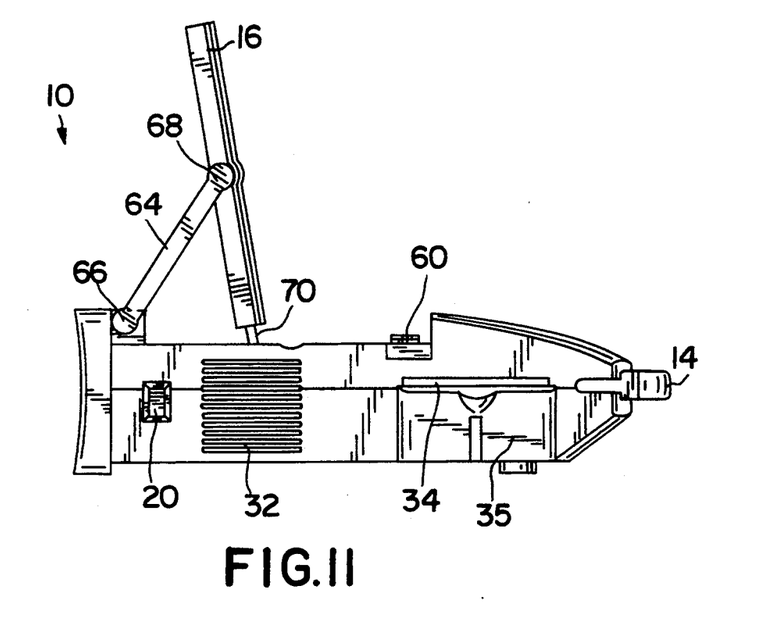
FIG. 11 is a side view of the apparatus of FIG. 1 with the display screen in a first angular viewing position.
Figure 12:
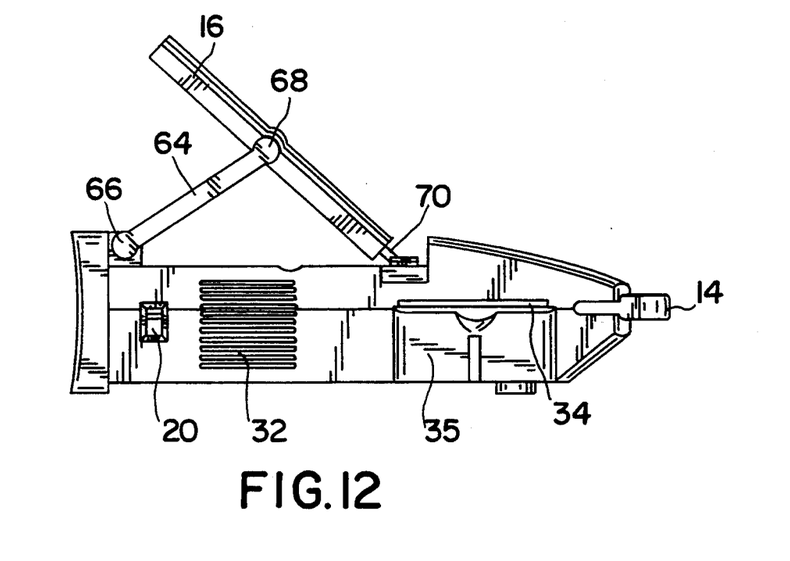
FIG. 12 is a side view of the apparatus of FIG. 1 with the display screen in a second angular viewing position.

FIG. 11 is a side view of programmer 10 with display screen 16 adjusted to the same viewing angle as in FIG. 8. FIG. 12 is a side view of programmer 10 where support member 70 has been brought forward as compared with FIG. 11, such that display screen 16 is adjusted to a less vertical viewing angle.

Figure 13:
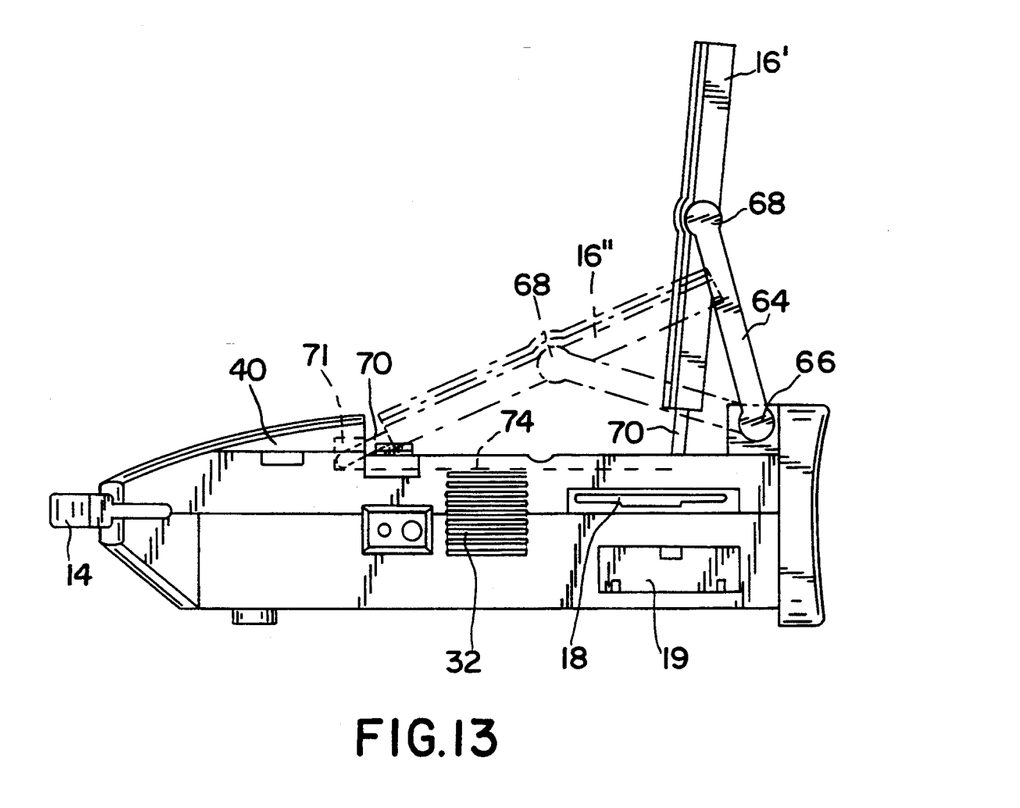
FIG. 13 is a side view of the apparatus of FIG. 1 showing the range of possible viewing positions of the display screen.

FIG. 13 depicts display screen 16 in its two most extreme viewing angles. In particular, display screen 16 is capable of being adjusted from the nearly vertical viewing angle designated 16' in FIG. 13 to the less vertical viewing angle 16" shown in phantom in FIG. 13. In the viewing angle designated as 16" in FIG. 13, support member 70 is received within a conforming recess 71 formed in the upper surface of housing 12 near the forward end of channel 74. It is to be understood, of course, that a plurality of viewing angles between the two extremes depicted in FIG. 13 are also available. In the presently preferred embodiment of the invention, indentations 76 in support channel 74 are arranged to provide for viewing angles of 19° (the angle designated as 16" in FIG. 13), 36°, 45°, 53°, 60°, 66°, 73°, 81° and 90° (the angle designated as 16' in FIG. 13), ±1°, from horizontal.

Figure 14A:
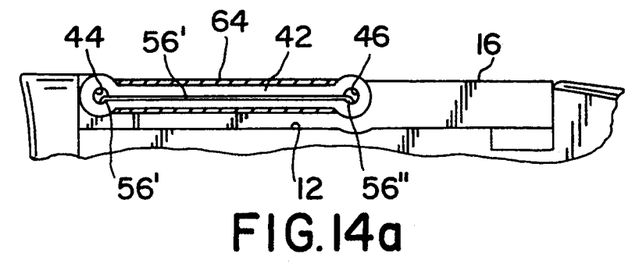
FIGS. 14a, 14b, and 14c are side views of the display screen of the apparatus from FIG. 1 in various open viewing positions.
Figure 14B:
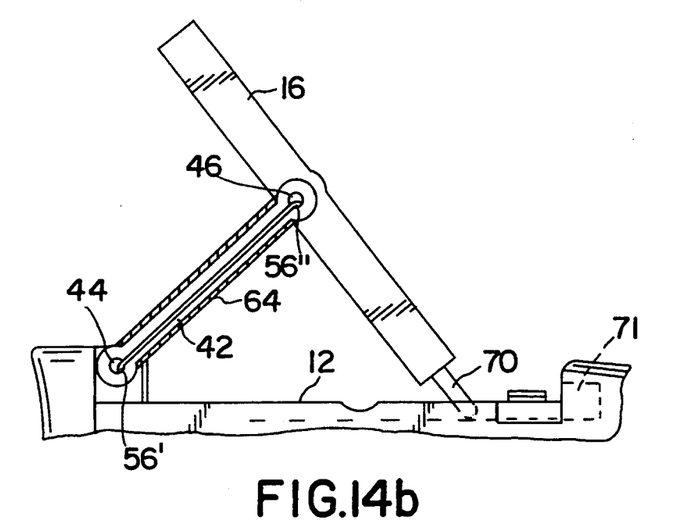
Figure 14C:
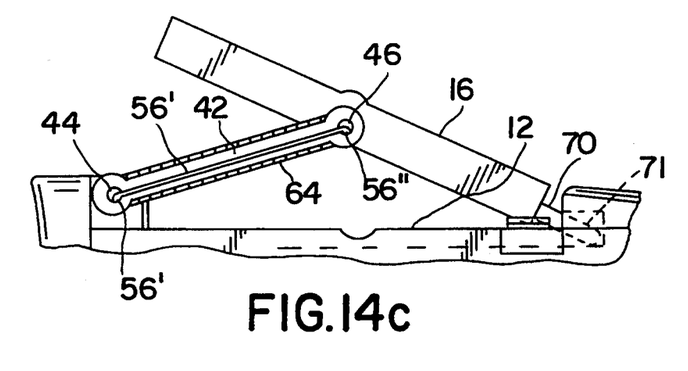

At least one of the two link arms 64 is preferably hollow, such that it can serve as a conduit for wiring necessary to couple display screen 16 to the computer circuitry disposed within housing 12. Referring to FIGS. 14a, 14b, and 14c, there is shown an illustration of a portion of programmer 10 including one of the link arms 64, display screen 16, and the upper surface of housing 12. In FIG. 14a, screen 16 is shown in the closed position as in FIG. 1. A cable 56 is coupled at one end, designated 56' in FIG. 14a, to computer circuitry (not shown) disposed within housing 12. Cable 56 is coupled at another end 56" to display screen 16, such that display screen 16 is capable of displaying graphics and text under control of the internal computer circuitry. As shown in FIG. 14a, cable 56 extends through hollow link arm 64. With screen 16 in the closed position of FIG. 14a, cable 56 is subjected to a 90° turn at stationary pivot point 44, and to less than a 90° turn at non-stationary pivot point 46.

In FIG. 14b, screen 16 is shown having been lifted up into one of its operational positions, with an approximately 45° viewing angle. It is to be noted that in all of the positions between the closed position of FIG. 5 and the 45° position of FIG. 14b, cable 56 is subjected to turns of less than 90° at stationary pivot point 44. In fact, with the screen in a 90° viewing angle (i.e., when screen 16 is completely vertical), cable 56 is substantially straight as it passes pivot point 44. In the 45° viewing angle of FIG. 14b, cable 56 is subjected to approximately a 90° turn at pivot point 46.

In FIG. 14c, screen 16 is shown having been positioned in its most extreme open position, which is the viewing angle designated as 16" in FIG. 13. In the viewing position of FIG. 14c, cable 56 is subjected to less than a 90° turn at pivot point 44 and less than a 180° turn at pivot point 46.

Thus, cable 56 is subjected to at most a 90° turn at pivot point 44, and at most a 180° turn at pivot point 46. This arrangement is believed to be advantageous, as it prevents undue fatigue of cable 56 that could result from subjecting cable 56 to more extreme turns.

Figure 15:
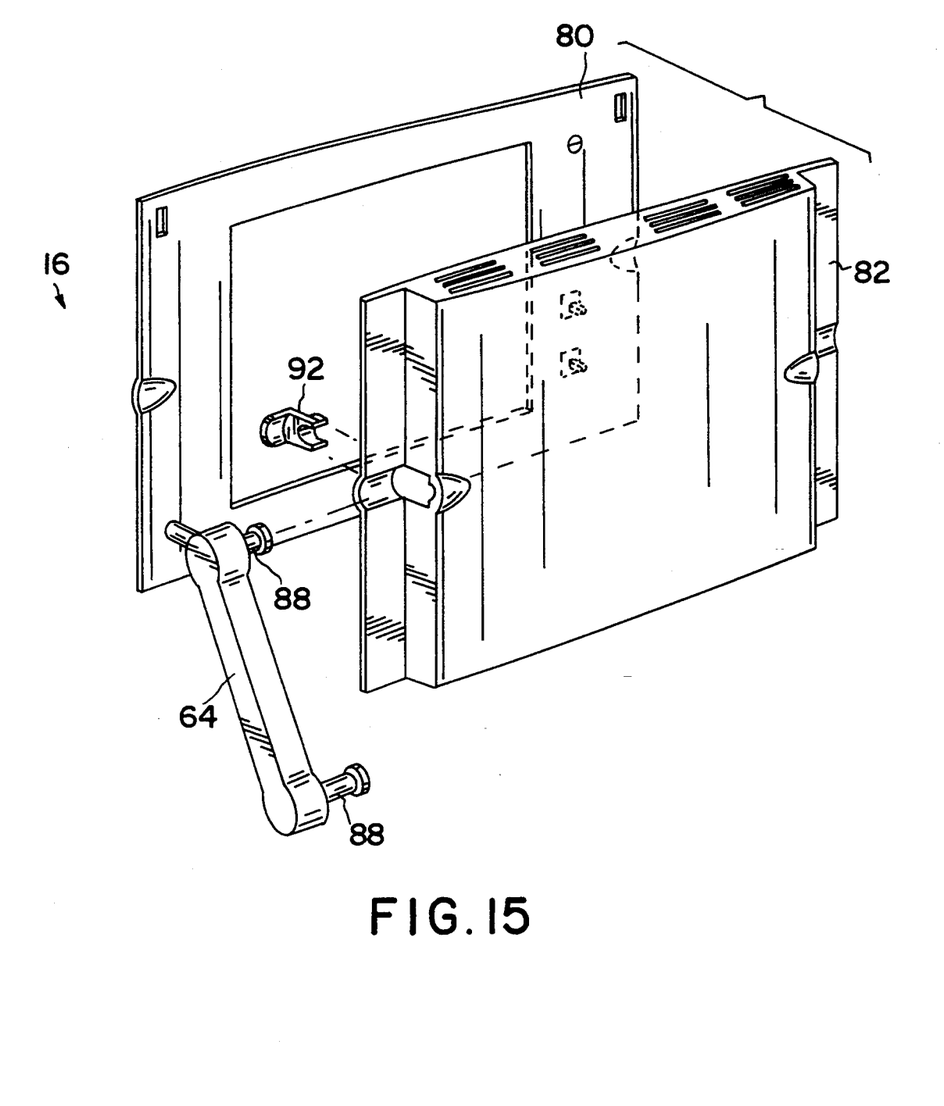
FIG. 15 is an exploded perspective view of the display screen of the apparatus of FIG. 1.

In FIG. 15, there is shown an exploded perspective view of display screen 16 and link arms 64. As shown in FIG. 15, display screen 16 comprises a front housing 80 and a rear housing 82 configured to house a display unit (not shown in FIG. 15), which as previously noted is preferably of the LCD or electroluminescent type. Link arms 64 are provided with flared projections 88 at each end. Projections 88 are received in an opening in rear housing 82 and pivotally secured therein by means of a securing member 92 adapted to engage flared projection 88 on the end of link arm 64.

As previously discussed, there are certain overall design considerations that are particularly relevant in the context of implantable device programming apparatuses. During implantable device programming, it is important that the operator be able to concentrate on the patient and the patient's well-being, rather than being distracted with the details of programmer operation. In order to ensure that operation of programmer 10 is intuitive and efficient, several components of programmer 10 are identified by simple pictorial representations or icons with readily apparent meaning. It is believed that the use of symbols in this manner is well known in the art. See, for example, U.S. Pat. Des. No. 295,631 to Wells-Papanek et al. entitled "Icon for Dividers or the Like"; and U.S. Pat. Des. No. 295,632 to Wells-Papanek et al. entitled "Icon for Wastebasket or the Like".

Figure 16A:
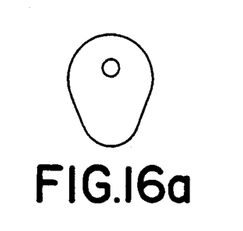
FIGS. 16a through 16r are illustrations of icons applied to components of the apparatus of FIG. 1.
Figure 16B:
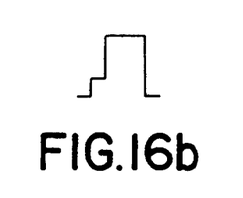
Figure 16C:
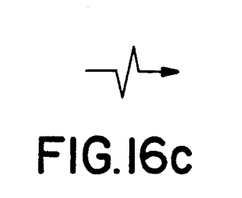
Figure 16D:
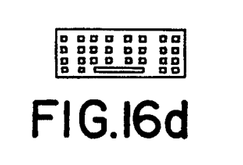
Figure 16E:
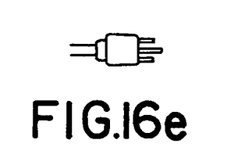
Figure 16F:
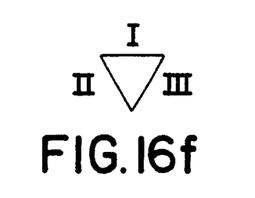
Figure 16G:
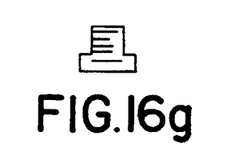
Figure 16H:
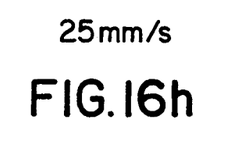
Figure 16I:
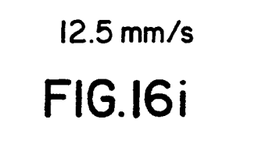
Figure 16J:
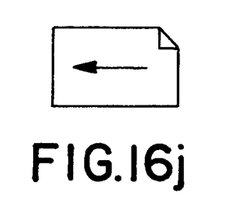
Figure 16K:
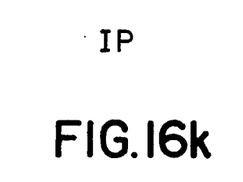
Figure 16L:
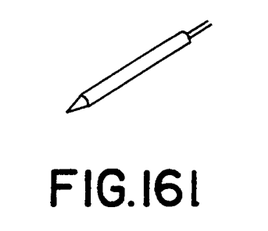
Figure 16M:
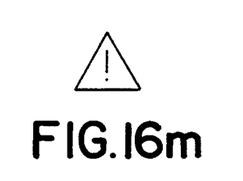
Figure 16N:
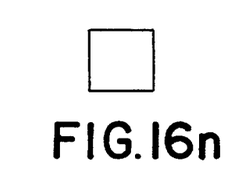
Figure 16O:
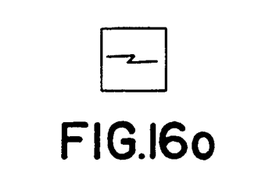
Figure 16P:
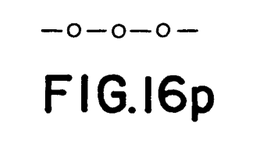
Figure 16Q:
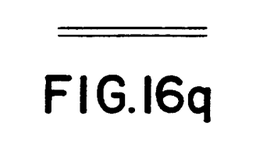
Figure 16R:
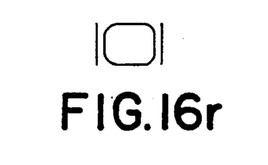

Referring to FIGS. 16a through 16r, a number of icons and symbols used to identify features of programmer 10 are shown. In the following Table 1, the meaning of each of the symbols in FIGS. 16a through 16r is set forth:

| FIG. | Meaning |
| --- | --- |
| 16a | programming head |
| 16b | calibrate |
| 16c | analog output |
| 16d | keyboard output |
| 16e | AC cable location |
| 16f | electrocardiogram (ECG) |
| 16g | printer |
| 16h | 25-mm/sec paper speed |
| 16i | 12.5-mm/sec paper speed |
| 16j | paper advance |
| 16k | interrogate / program |
| 16l | stylus connector |
| 16m | warning -- see reference manual for information |
| 16n | emergency switch |
| 16o | deliver stimulating pulse |
| 16p | serial data port |
| 16q | parallel data port |
| 16r | VGA graphics port |

The icons of FIGS. 16a through 16r are applied at various appropriate locations on programmer 10 so that the features or components to which they refer can be quickly identified and located. For example, the icon of FIG. 16n is a solid red square that is applied to an emergency button, designated as 94 in FIG. 8. Emergency button 94 is prominently located near the front of programmer 10, and it is believed that the solid red color renders button 94 easily identifiable and readily locatable. When emergency button 94 is pressed, programmer 10 enters into an emergency mode of operation, a mode commonly provided for in prior art programmers. Similarly, the "deliver stimulating pulse" icon in FIG. 16o is applied to a button, designated 96 in FIG. 8, which when actuated initiates delivery of a stimulating pulse by an implanted device in telemetric communication with programmer 10.

Referring to FIGS. 8 and 9, an LED 97 or similar visual indicator is visible near the upper left-hand corner of display screen 16. LED 97 functions to provide an indication that programming head 42 is properly positioned above the implant site to allow telemetric communication between programmer 10 and the implanted device. In one embodiment of the invention, LED 97 is actually disposed within the front and rear housings (80 and 82) of screen 16 and is visible through a semi-transparent light-tunnel or bezel disposed in an small hole opening in front housing 80. The programming head icon of FIG. 16a may be associated with LED 97 to identify this position indicating function of LED 97; in addition, it is contemplated that the bezel itself may be in the shape of the programming head to identify the function of LED 97. It is contemplated that LED 97 may be of the well-known two-color type, in order to distinguish between marginally suitable programming head positioning and more optimal positioning.

Also with reference to FIGS. 8 and 9, an "ink-well" type indentation 99 formed near the lower right-hand corner of display screen 16 to provide a resting place for stylus 44.

From the foregoing detailed description of a specific embodiment of the invention, it should be apparent that a portable computer apparatus having an articulating display screen adjustable to a plurality of viewing angles has been disclosed. Although a specific embodiment of the invention has been disclosed in some detail, it is to be understood that this has been done for the purposes of illustration only, and is not intended to limit the scope of the present invention as defined in the accompanying claims. It is contemplated that various alterations, substitutions, and modifications can be made to the embodiment of the invention described herein without departing from the spirit and scope of the invention as defined in the claims. For example, although the present invention has been described herein in the context of a programming apparatus for use in conjunction with implanted medical devices and the like, it is believed that the present invention may be equally advantageously practiced in conjunction with many other types of portable computer equipment.

What is claimed is:

1. A portable computer apparatus, comprising:
    a main housing having an upper surface and containing computer circuitry;
    a display screen having side edges and upper and lower edges;
    a link arm coupled between said main housing and said display screen, said link arm pivotally coupled at one end thereof to said main housing and pivotally coupled at a second end thereof to said display screen, at a location spaced from said lower edge to enable said screen assembly to articulate relative to said housing;
    an engagement mechanism disposed between said display screen and said housing cooperating to stably maintain said screen at any of a plurality of viewing angles, said housing provided with a support channel located centrally on said upper surface of said housing, said engagement mechanism comprising a support member extending from a central location on said lower edge of said display screen, engageable with said support channel.

2. An apparatus in accordance with claim 1, wherein said link arm is coupled to said display screen along a side edge thereof.

3. An apparatus in accordance with claim 1, wherein said support channel defines a plurality of detents therein for engaging said support member.

4. An apparatus in accordance with claim 1, wherein said engagement mechanism comprises a support member adapted to be frictionally engaged in said support channel.

5. A portable computer apparatus, comprising:

a main housing, having an upper surface, said main housing containing computer circuitry;

a display screen having a substantially flat display surface and having top, bottom, left and right edges;

left and right link arms coupled between said main housing and said display screen, said left link arm pivotally coupled at one end thereof to said main housing upper surface and pivotally coupled at a second end thereof to said left side of said display screen, said right link arm pivotally coupled at one end thereof to said main housing upper surface and at a second end thereof to said right side of said display screen;

a support member, extending from a central portion of said bottom edge of said display screen;

a support channel disposed on a central portion of said main housing upper surface, extending from a forward location to a rear location thereon, said support channel adapted to engage said support member at a plurality of locations therein;

said display screen movable from a closed position wherein said display surface faces and is substantially parallel to said main housing upper surface, to any of a plurality of different viewing angles, said support member being engaged at a different location in said support channel for each of said different viewing angles.

6. The apparatus of claim 5, further comprising:

left and right latch mechanisms, disposed on said main housing upper surface and adapted to secure said display screen in said closed position.

7. The apparatus of claim 5, further comprising:

a carrying handle, disposed on a forward end of said apparatus;

a storage compartment having a hinged cover which defines a portion of said upper surface;

a power cable compartment having a hinged cover, disposed on a rear end of said apparatus.

8. The apparatus of claim 5, wherein at least one of said link arms is hollow, and wherein a wire for conducting an electrical signal from said computer circuitry to said display screen passes through said at least one hollow link arm.

* * * * *